United States Patent
Sabah et al.

(10) Patent No.: US 7,855,564 B2
(45) Date of Patent: Dec. 21, 2010

(54) ACOUSTIC WAVE DEVICE PHYSICAL PARAMETER SENSOR

(75) Inventors: Sabah Sabah, Nashua, NH (US); Jeffrey C Andle, Falmouth, ME (US); Daniel S Stevens, Stratham, NH (US)

(73) Assignee: Delaware Capital Formation, Inc., Wilmington, DE (US)

( * ) Notice: Subject to any disclaimer, the term of this patent is extended or adjusted under 35 U.S.C. 154(b) by 357 days.

(21) Appl. No.: 12/031,055

(22) Filed: Feb. 14, 2008

(65) Prior Publication Data

US 2009/0206844 A1    Aug. 20, 2009

(51) Int. Cl.
*G01R 19/00*   (2006.01)
(52) U.S. Cl. .............. 324/600; 324/636; 324/76.11; 324/658
(58) Field of Classification Search ............ 324/632, 324/633, 636, 600, 658, 76.11
See application file for complete search history.

(56) References Cited

U.S. PATENT DOCUMENTS

| | | | |
|---|---|---|---|
| 4,218,298 A | 8/1980 | Shimada et al. | |
| 4,625,208 A | 11/1986 | Skeie et al. | |
| 5,024,088 A | 6/1991 | Komatsu et al. | |
| 5,610,335 A | 3/1997 | Shaw et al. | |
| 5,694,095 A * | 12/1997 | Mineyoshi | 333/193 |
| 5,813,280 A | 9/1998 | Johnson et al. | |
| 6,237,417 B1 | 5/2001 | Lonsdale et al. | |
| 6,556,146 B1 | 4/2003 | Ruile et al. | |
| 2006/0137453 A1 | 6/2006 | Wu et al. | |
| 2006/0226933 A1 * | 10/2006 | Takahashi | 333/195 |
| 2007/0069264 A1 * | 3/2007 | Subramanyam et al. | 257/295 |

OTHER PUBLICATIONS

Nakamura, Kentaro et al., "A Novel Magnetic Field Sensor Using Piezoelectric Vibrations", IEEE Ultrasonics Symposium, 2006, pp. 1429-1432.
PCT Search Report dated Mar. 8, 2009 of Patent Application No. PCT/US2009/033016 filed Feb. 4, 2009.

* cited by examiner

*Primary Examiner*—Vincent Q Nguyen
(74) *Attorney, Agent, or Firm*—Vern Maine & Associates

(57) ABSTRACT

An acoustic wave sensor employs an electromagnetic device (EMD) to transduce and amplify the response of an impedance element to a physical measurand. A measurand is defined as a physical parameter being quantified by measurement. One embodiment uses a magnetic field sensor employing a microelectromechanical system (MEMS) capacitor to affect a change in the response of a SAW filter.

7 Claims, 13 Drawing Sheets

ACOUSTIC WAVE DEVICE PHYSICAL PARAMETER SENSOR

FIELD OF THE INVENTION

The invention relates to parameter sensing, and more particularly, to a sensor that employs an electromagnetic device (EMD) to convert changes in an impedance element related to a physical measurand into an instrumentable signal. Measurand is defined as a physical parameter being quantified by measurement.

BACKGROUND OF THE INVENTION

Existing sensors rely on phenomena that do not support high sensitivity, remote monitoring of parameters such as magnetic fields and the like. For example, Hall Effect sensors detect the voltage generated by the drift of charge carriers when a magnetic field is applied to a current. Other sensors rely on detecting the Lorentz force of a magnetic field on a current carrying wire. Still others such as magnetostriction layer sensors incorporate the lengthening effect on ferromagnetic materials such as cobalt and Terfenol-D® magnetostrictive alloy when exposed to magnetic fields. Terfenol-D® is a registered trademark of Edge Technologies, Inc.

Magnetoresistive element sensors or ordinary magnetoresistive sensors commonly incorporate flux concentrators and measure the decrease in resistance as a function of applied magnetic field. Other sensors incorporate effects such as giant magneto-impedance (GMI). GMI, employs, for example, a NiFe coated BeCu wire. High frequency current is passed through the wire and the resistance component of its impedance is measured. This resistance measurement reflects the presence of magnetic fields. These sensors can be very temperature dependent, resulting in either poor accuracy or expensive correction measures. Such sensors therefore have disadvantages regarding size, price, power, and data output access.

Other physical parameters are readily measured in the current art. Temperature is typically measured through the voltage caused by the Seebeck effect of a thermocouple, by the resistance change of a resistance-temperature device (RTD), or by the change in current-voltage properties of a semiconductor diode junction.

Electric fields are measured through direct measurement of potential between two conductive probes (voltmeter) of known spacing and through non-linear effects (second order effects) on devices through modulation of an elastic constant (electro acoustics) or conduction band bending (semiconductors).

The AWD based measurements offer a universal method to the measurement of a physical parameter as it affects an electrical lumped element, the element then allowing a number of physical structures and interactions with a physical measurand.

What is needed, therefore, are techniques for sensing that provide for very small size, low price, low-power operating range, passive, wireless, and contactless method of measurement and remote interrogation.

SUMMARY OF THE INVENTION

The advantages of combining an external impedance element with an acoustic wave device include very small size, low price, a low power operating range, passive operation i.e. no battery, and the ability to be individually interrogated from a distance with a microwave reader.

A sensor is presented that employs an electromagnetic device (EMD) and a load impedance element to transduce a physical field or parameter into an instrumentable measurement. The load is a lumped or distributed impedance element, by way of non-limiting example a capacitor, inductor, resistor, or resonator, that is responsive to external physical parameters, such as pressure, temperature, strain, stress, acceleration, acoustic vibration, chemical concentration, biochemical concentration, viscosity, density, elastic modulus, electric fields, or magnetic fields. The EMD, for example, can be an acoustic wave device (AWD) employing acoustic waves to obtain a highly stable electrical property, such as a phase shift, resonant frequency, insertion loss or the like, the property being responsive to the value of the physically-responsive load element.

One embodiment of the present invention provides an AWD configured as a one port resonator having a series electromechanical resonance in parallel with the static capacitance of the transducer in accordance with the well known Butterworth-Van Dyke (BvD) equivalent circuit model. In parallel with the resonator is an impedance element responsive to a physical parameter. The resonator is connected to an antenna and is interrogated wirelessly though means known in the art. At a frequency slightly above the series resonance frequency of the electromechanical portion of the circuit, the mechanical inductance forms a parallel resonant circuit with the static transducer capacitance. The parallel resonance allows an electrical signal to be received from an antenna, stored in the resonator and slowly reradiated as a backscatter signal. The frequency of the backscatter signal is modified by changes to the parallel coupled impedance element. For example, a capacitance placed in parallel with the AWD transducer capacitance and physically responsive to magnetic fields offers one such sensor mechanism.

In an illustrative embodiment, a two-port AWD is employed wherein the energy is inserted into a first port and is reradiated as a backscatter signal from the first port. The frequency of optimum signal backscatter is perturbed by the electrical load applied to the second port.

Other embodiments can include various physically reactive devices such as thermistors, semiconductors, deformable capacitors, piezoresistors, and the like used to load or interconnect one or more sampling ports. In the case of resonators, one can employ an AWD in which energy is inserted and reradiated from the same port—a configuration that shall be referred to as a reflective sensor regardless of the number of physical ports in the AWD. Resonators can also be configured with an AWD in which energy inserted into one port is detected at another port—a configuration that shall be referred to as a transmissive sensor. Both reflective and transmissive sensors may incorporate at least one additional port to which a physically responsive impedance element (a probe) is operably connected. Operably coupled or connected includes inductively and capacitively coupled elements and that a direct conductive connection is not required.

For a resonant sensor, the excitation and instrumentation seek to detect and estimate a resonant frequency and a limited number of probes may be simultaneously connected to provide meaningful and identifiable data. Another class of sensors employs broadband time domain methods, such as a tapped reflective delay line used in radio frequency identification. In this case, each tap location offers an opportunity to place an interdigital transducer operably connected to a probe. Multiple probes may be employed to modulate the reflection of an operably connected tap, each tap resulting in a perturbation to the transmitted or backscattered signal at a relative time from interrogation corresponding to the physical tap location.

Embodiments include a system for measuring a physical measurand having at least one variable impedance element probe responsive to at least one measurand and at least one electromagnetic device (EMD) having at least one port, where the probe is operably connected to the port, and the EMD is electrically responsive to the response of the probe. Another embodiment further comprises a wireless interrogation device configured to measure the EMD.

In yet another embodiment, the EMD is selected from the group consisting of cavity resonators, optical fiber delay lines, microwave cavity resonators, dielectric resonators, acoustic wave delay lines, acoustic wave resonator devices, magnetostatic wave (MSW) delay lines, MSW resonators, charge-coupled device (CCD) delay lines, acoustic charge transport (ACT) devices, stripline resonators, surface plasmon resonators, integrated optics resonators, and tunable laser optical resonators.

In an embodiment, the EMD is at least one acoustic wave device (AWD). In another embodiment, the AWD is a stored energy resonator. The AWD can be configured to reradiate electrical energy incident on an input port. AWDs can also comprise an input port and at least one sensing port, where the probe is operably connected to the sensing port. The AWD can also be a reflective-tap delay line comprising reflective taps, where at least one of the reflective taps comprises at least one interdigital transducer (IDT), and the IDT comprises at least one sensing port. Embodiments can further comprise a plurality of reflective taps, providing an identification sequence specific to the system.

Further embodiments provide that each AWD comprises an input port and at least one sensing port, where at least one probe is operably connected to at least one sensing port; and at least one probe is a variable capacitor responsive to magnetic fields.

Another embodiment provides that each AWD comprises an input port and at least one sensing port, where at least one probe is operably connected to at least one sensing port; and at least one variable impedance element probe is a variable capacitor responsive to pressure.

In yet further embodiments, the physical measurand is selected from the group consisting of magnetic field, electric field, pressure, strain, stress, temperature, acoustic vibration, acceleration, chemical concentration, biochemical concentration, viscosity, density, and elastic modulus.

In other embodiments, the variable impedance element probe is a variable capacitor, where the capacitance value changes in response to motion of one or more elements of the variable capacitor. In embodiments, the variable capacitor is selected from the group consisting of: a comb capacitor, a cantilever capacitor, and a suspended membrane capacitor.

In yet other embodiments, the variable impedance element probe is selected from the group consisting of: a chemically responsive resistance, a chemical field-effect transistor (Chem-FET), and a metal-oxide-semiconductor field-effect transistor (MOSFET). In another embodiment, the variable impedance element probe is an acoustic wave device (AWD) resonator.

In embodiments, a component material of the variable impedance element probe is selected from the group consisting of Fe, Ni, Co, magnetite, and ferromagnetic alloy.

Another embodiment is a method for measuring a physical measurand comprising the steps of changing the impedance of a variable impedance element probe resulting from a physical measurand; changing attributes of an acoustic wave device (AWD) from the impedance change; interrogating the AWD; receiving a response signal from the AWD; and determining the value of the physical measurand from the received signal. The embodiment's interrogating step can comprise a circuit selected from the group consisting of an oscillator circuit, a transmission circuit, a reflection circuit, and a passive wireless interrogation circuit.

Yet another embodiment is a sensor device comprising an electromagnetic device (EMD) comprising at least one electrical port; at least one variable impedance element probe that is operably coupled to at least one electrical port, where at least one probe is configured to be responsive to at least one physical measurand, and the EMD is electrically responsive to a value of at least one probe, a value of the EMD response being representative of the physical parameter.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
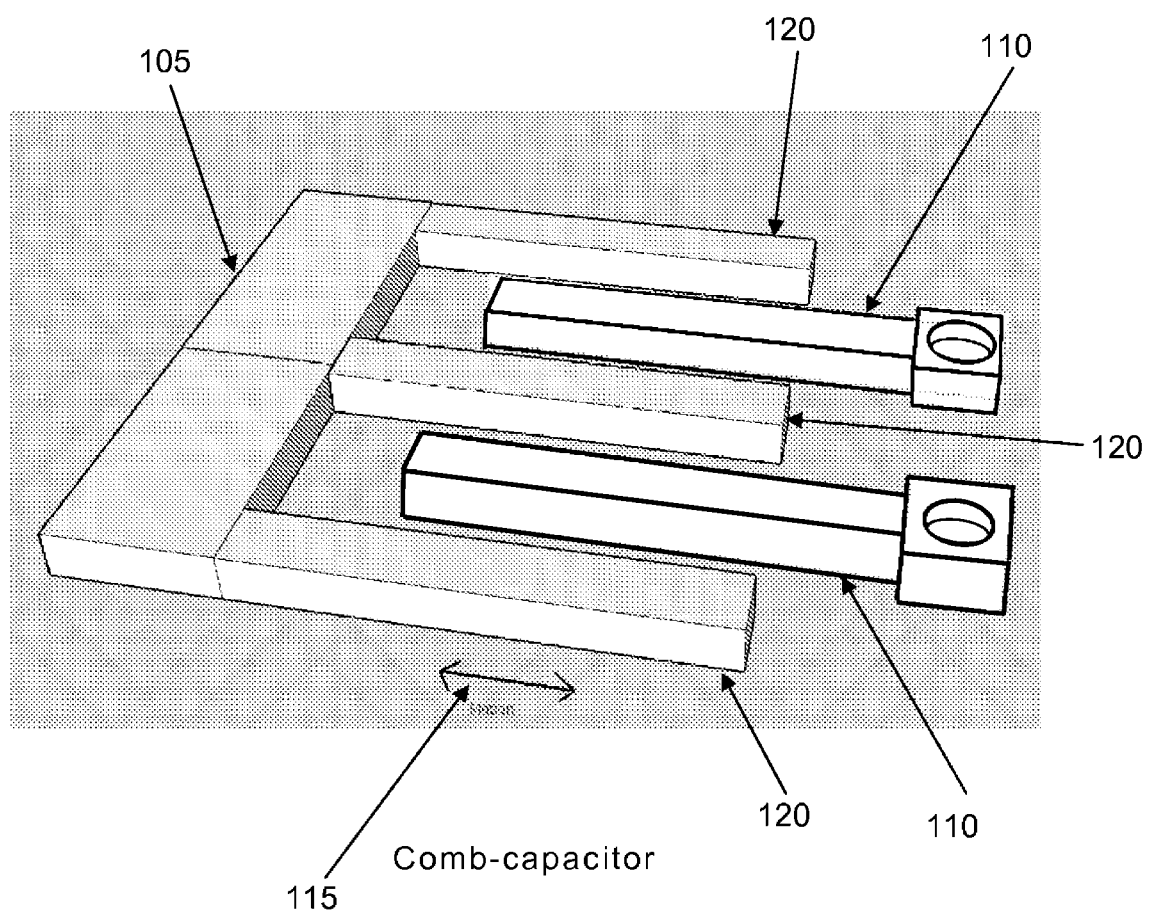
FIG. 1 is a perspective view illustrating a schematic of a comb capacitor configured in accordance with one embodiment of the present invention.

The present invention relates to a class of components collectively denoted as electromagnetic devices (EMDs). These interface with an electrical circuit and store a replica of an electrical signal. EMDs currently exist that suit the requirements of the invention using optical, magnetostatic, acoustic, and radio frequency waves in both delay line and resonant structures. However, other implementations are readily available and this is not an exhaustive list of the possible implementations.

As will become clear through the remainder of the application, there are constraints for an EMD to satisfy to be useful in the invention. Examples such as acoustic wave devices (AWDs) illustrate embodiments of the invention employing suitable EMDs.

The present invention provides a system that exhibits a large response to physical parameters. Many physical parameters have well-characterized effects on simple impedance elements such as resistors (strain gauges, thermistors and the like), capacitors (through change in effective dielectric thickness or constant), inductors, and so forth. However, the direct measurement of the impedance of these devices may be impractical. In some cases, the changes in the physical parameter induce changes in impedance that are below the resolution of simple capacitance meters and the like. In other cases, the values of impedance are too high to be accurately measured with simple embedded instrumentation.

The invention addresses these issues by providing a transduction component operably connected to the impedance element sensor. A change in impedance alters the electrical properties of an EMD. This is designed to provide a more readily instrumented change in electrical parameters.

In one example, a resonator provides a measurable resonant frequency that is responsive to variations in the value of the impedance element. Measurement of changes of this frequency requires the ability to accurately instrument the resonant frequency of the resonator. This places constraints on the ratio of center frequency to bandwidth (Q) of the resonator when it is loaded by the instrumentation system. The loaded Q may be at least 100, or over 1000.

In another example, a delay line provides a time-delayed replica of an interrogation signal. The time delay to the replica or the amplitude of the replica may be designed to be responsive to changes in impedance of the operably connected sensor element. The minimum interval to which the delay time may be measured is inversely proportional to the frequency. The amount of information is proportionate to the time-frequency product. The measurements can be based on standard factors such as the 3 dB point, for example. The product is analogous to the loaded Q of the resonator. Frequency-time products may be at least 100, or over 1000.

The Q of the resonator, as loaded by the interrogation circuit and the impedance element, and the frequency-time product of the delay line shall collectively be designated as a figure of merit (FOM) of the EMD.

Embodiments of the invention can allow passive wireless monitoring of the impedance of a simple sensor element. This can be accomplished by using the resonant properties of an EMD resonator, or the phase (or delay or peak frequency) of an EMD delay line to provide a meaningful back-scatter response to an electrical signal. This objective can place requirements on the frequency-time product of the EMD. In addition, frequency selection may be limited by prevailing legislation specifying allowed frequency bands in each country of operation. These are typically hundreds of MHz to several GHz. For illustration, a value of 1 GHz will be assumed in examples.

Ease of measurement of the backscatter signal from the passive sensor requires delay times (for delay lines) on the order of 1 µs. This results in a frequency-time product on the order of 1000. For resonant backscatter systems, the ringdown time (inverse of the bandwidth of the resonator) should be on the order of 1 µs to allow sufficiently accurate frequency estimation; again resulting in a loaded Q of approximately 1000.

For illustration, one might consider a length of simple transmission line, e.g. coaxial cable, with the interrogation signal applied at one end and the impedance element providing a termination at the distant end of the transmission line. Obtaining a frequency-time product of 100 at 100 MHz would require 1 µs of delay. This would involve nearly 150 meters of coaxial cable to obtain the round trip delay of a reflected signal. Implementing a stub resonator from the coaxial cable could be accomplished as well. However, the losses of the cable would limit the functionality. Similarly, electromagnetic and radio-frequency resonators based on stripline and the like are also potential means of implementing an EMD and may have size advantages.

Equipping an optical fiber with an electrical to optical converter would also be possible. The propagation loss objection could be overcome. However, the physical size would still have an impact. Integrated optics may allow optical integrated circuits with sufficient delay times and propagation losses and such are considered as EMDs.

Embodiments providing the discussed figure of merit in a physically practical size include, by way of non-limiting example: acoustic wave delay lines and resonator devices (AWDs), magnetostatic wave (MSW) delay lines and resonators, charge-coupled device (CCD) delay lines including acoustic charge transport (ACT) devices, dielectric resonators, stripline resonators, surface plasmon resonances, integrated optics resonators (including optical resonators as might exist in a tunable laser), and the like. The use of AWDs in the examples represents illustrative embodiments.

Generally, the resonant structures provide a single signal output (e.g. frequency) to a single impedance sensor element. Delay line devices however may have a multitude of ports providing a multitude of delayed replicas of the signal. A portion of these may be operably connected to a plurality of sensor elements while another portion of these may be hard-coded to provide an identification sequence specific to the sensor, as is known in the field of radio frequency identification (RFID).

In other embodiments, the class of impedance elements offering desirable properties includes semiconductor sensors. The transfer impedance of such devices as bipolar transistors and field effect transistors (FETs) represent a convenient means by which to provide an impedance related to a physical parameter. For example, direct photoconductivity of bulk semiconductors as well as the optical switching of bipolar phototransistors provides a resistance determined by the flux of photons on an impedance-based sensor.

In yet other embodiments, a thin semiconductor channel in a field effect transistor offers a resistance that is directly responsive to electric fields. Such a structure offers a very high impedance (capacitively coupled) measure of an applied voltage, converting said voltage to a resistance. A chemical-responsive embodiment uses chemiresistive sensors based on the modulation of resistance of a semiconducting polymer or semiconducting metal oxide by a chemical surface or bulk reaction. This demonstrates use of a bulk conductivity property.

Chemical field-effect transistor (Chem-FET) embodiments employ a chemically selective electrode on an isolated gate contact to electrochemically generate a potential that modulates the transfer resistance of the field effect transistor (FET). Such a Chem-FET operably connected to an EMD allows remote passive interrogation of the chemical state of an inaccessible location.

An embodiment of the acoustic wave sensor disclosed employs an acoustic wave device (AWD) to transduce and amplify the response of an operably coupled impedance element (probe) physically responsive to a physical measurand. One illustrative embodiment uses a magnetic field sensor employing a microelectromechanical system (MEMS) capacitor to affect a change in the response of a surface acoustic wave (SAW) filter.

Other physical effects such as pressure, strain, stress, temperature, electric field, acoustic vibration, acceleration, viscosity, elastic modulus, density, chemical concentration, biochemical concentration, and the like could equally well be used to affect the impedance change. The list of target physical measurands is meant to be illustrative and not exhaustive. Specific measurands such as pH, humidity, total acid number, total base number, and the like represent chemical concentrations. Specific measurands such as torque and flexure are variants of stress and strain.

Other AWD devices such as resonators and delay lines using SAW or other acoustic waves can also be employed in place of a SAW filter. AWDs may include Si AWDs, MEMS AWDs, and the like. The use of acoustic waves in the examples is illustrative embodiments; other resonators or delay lines may be configured to be suitably interrogated and responsive to the impedance elements. Alternative electromagnetic devices (EMDs) are contemplated where an AWD is referenced. Alternate embodiments using other EMDs might include optical fiber delay lines, microwave cavity resonators, dielectric resonators, and the like.

The operably connected capacitor of the variable capacitor—SAW filter embodiment demonstrates sensitive changes in value when a magnetic field is applied. The acoustic wave device component is designed to be sensitive to an external parallel or series connected capacitor. The theoretical simulation and measured results demonstrate good magnetic field sensor performance. This includes relatively wide band linear correlation between the applied magnetic field and the overall parameters of the AWD, including magnitude of the transmission function and center frequency when employing a filter or a resonator component. The same approach can also be used to detect ferromagnetic materials.

There are multiple embodiments that implement a magnetic field sensitive capacitor. Basically, the capacitance value is changed by changing the distance between two plates, the distance change caused by a magnetic field. The capacitor's value changes, generally, in response to motion of one or more elements of the variable capacitor. In other embodiments, the "capacitance" term can be any physically responsive impedance element. This approach can demonstrate a method to wirelessly interrogate a low-Q acoustic wave sensor; using it as the impedance element loading a high-Q, passive wireless sensor. The following mechanical structure illustrative embodiments can be used to implement magnetic field sensitive capacitance components.

In FIG. 1, a comb capacitor Micro-Electro-Mechanical-system (MEMS) embodiment 100 is used to realize the load capacitor. Both the comb as well as cantilever and bridge embodiment structures can be used to realize the load capacitor values. Advantages of using MEMS structures include low price and size and the ability to incorporate the structure on an integrated circuit.

Note that SAW modeling allows one to calculate the capacitance of a comb structure since a similar structure is used in SAW interdigital transducers; this does not mean that only SAW-type sensors are used. It means that the absolute value of the external capacitor in this embodiment can be determined by using simple SAW inter-digital transducer (IDT) analytical expressions or computer aided design methods, or it can be physically measured. This capacitance value is then correlated to the sensed parameter value. Simulation results of an external capacitor in parallel connection with a one port resonator, as in FIG. 2, show that the frequency shift at minimum insertion loss at resonant frequency gives a clear, linear, behavior of change in capacitance between 0.1 pF and 10 pF when operably coupled to a 2326 MHz SAW resonator filter.

Capacitance structure embodiments can also be used to sense pressure. For example, a part of the comb—MEMS inter-digital finger can be realized as movable fingers 120, as in FIG. 1 by way of non-limiting example. By applying a magnetic field or pressure to the movable part 105 of the comb capacitor 100, fingers 120 move 115 with respect to fingers 110. This causes the overlap area between fingers 110 and 120 to change. As is well-known, different overlap areas result in different capacitance values. The capacitor structure, regardless of its construction, can be connected to the surface acoustic wave device to sense change based on different environmental values.

Figure 2:
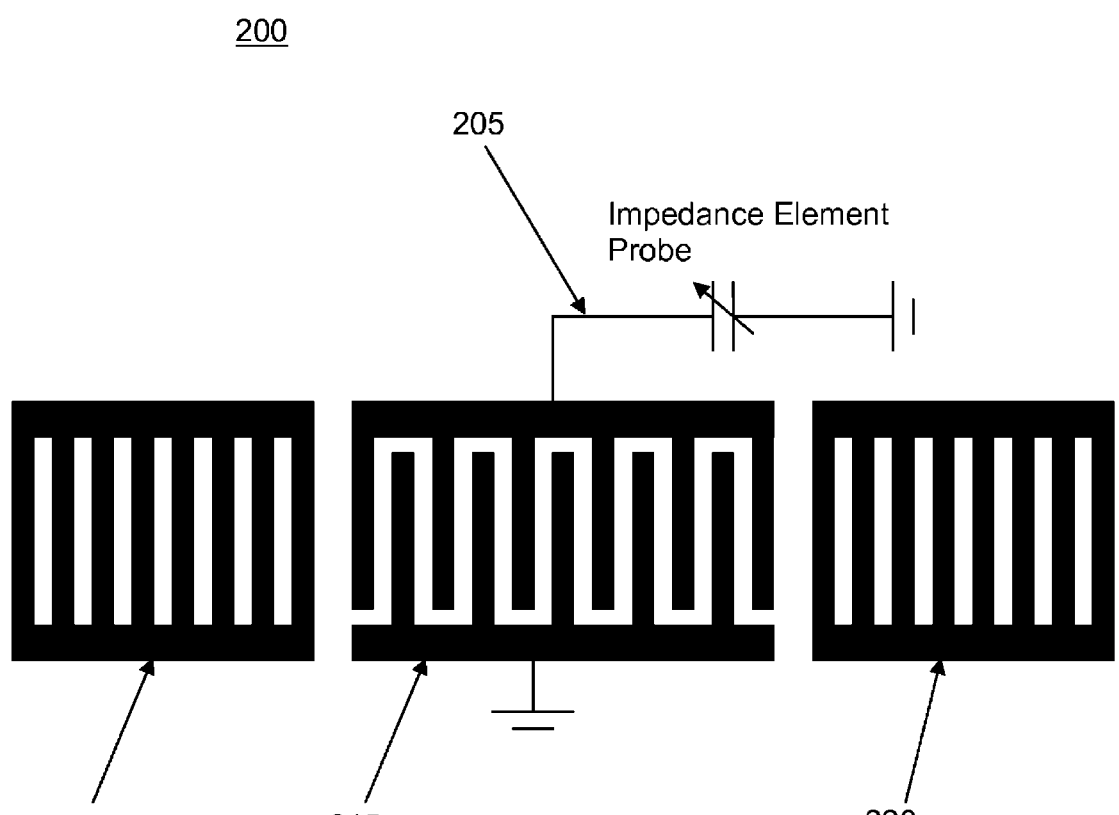
FIG. 2 is a diagram illustrating a one port surface acoustic wave (SAW) resonator with an external probe configured in accordance with one embodiment of the present invention.

FIG. 2 illustrates an embodiment 200 having an operable connection between a surface acoustic wave one port resonator 215 with external impedance element probe 205. Note that the component indicated by the variable capacitor symbol 205 is illustrative only and any two-terminal impedance element or network may be employed. Other figures include a variable impedance symbol. The variable impedance symbol is meant to include variable capacitors. As previously stated, note also that operably coupled or connected includes inductively and capacitively coupled elements and that a direct conductive connection is not required. This configuration with reflectors 210, 220 maximizes sensitivity but may incur a variation of the input matching conditions. Therefore, in some applications, it may be desirable to employ a "two port" sensing element as in FIGS. 3A and 3B.

Figure 3A:
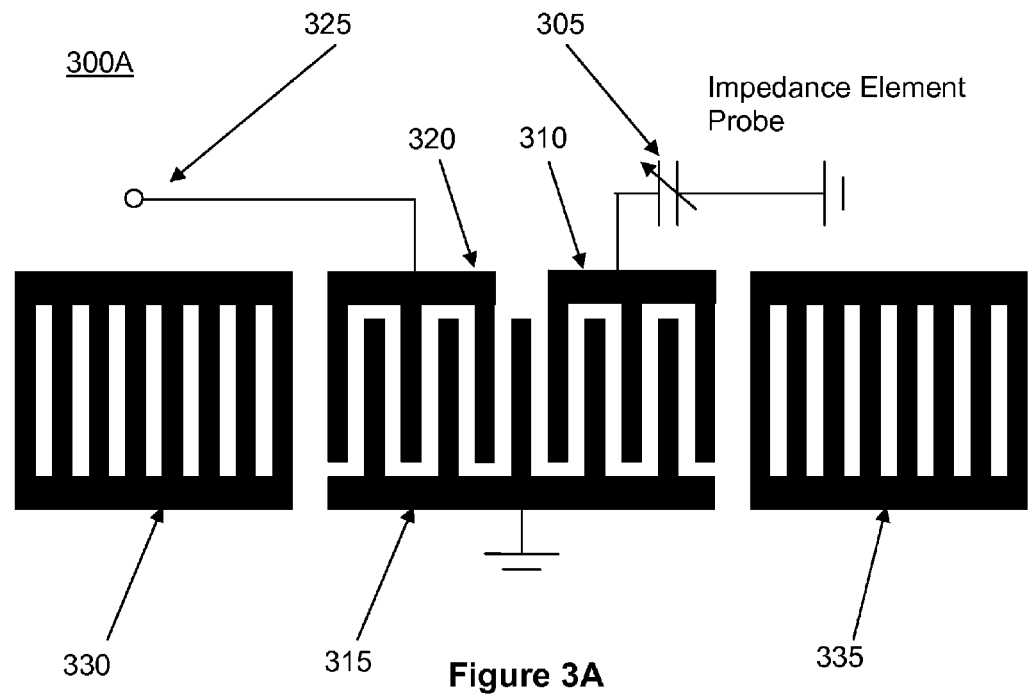
FIG. 3A is a diagram illustrating a two port SAW resonator with an external probe configured in accordance with one embodiment of the present invention.

FIG. 3A displays an embodiment 300A with a connection between a surface acoustic wave two port resonator IDT 315 and reflectors 330, 335, and an external impedance element probe 305. The impedance element probe 305 is the termination to the second port 310 and the first port 320 is employed as the instrumentation port 325. This arrangement offers a relatively stable load impedance characteristic to the instrumentation but allows the resonant frequency or time delay to be modulated by the parameter-dependent impedance. The external impedance element probe 305 can alternatively be connected between the input 320 and output 310 ports also. As before, component 305 can be any two-terminal impedance element or network.

Figure 3B:
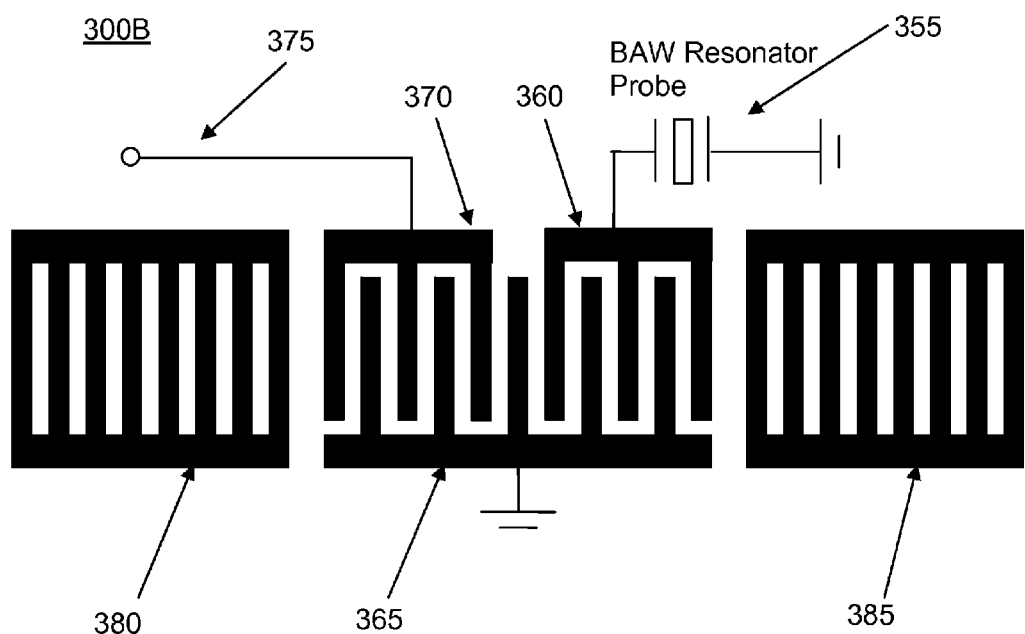
FIG. 3B is a two-port saw resonator operably coupled to a bulk acoustic wave (BAW) resonator AWD probe.

FIG. 3B displays an embodiment 300B also with a connection between a surface acoustic wave two port resonator IDT 365 and reflectors 380, 385, and an external impedance element probe 355. Similarly, the impedance element probe 355 is the termination to the second port 360 and the first port 370 is employed as the instrumentation port 375. In this embodiment, however, the probe 355 is an AWD, specifically, a bulk acoustic wave (BAW) resonator. The parallel resonant frequency of the BAW sensor is designed to coincide with the resonant frequency of a resonant AWD or the IDT center frequency of a delay line style AWD. The unloaded BAW sensor is initially primarily reactive and induces a pure reflection coefficient in the associated tap. Depending on the design of the AWD, and in particular of the tap, perturbation of the probe will result in a change in phase or magnitude of the reflected signal. The AWD can be designed to have good energy storage time (quality factor) as required by a passive wireless sensor system, regardless of the widely varying resonator quality of the probe BAW resonator.

Figure 4:
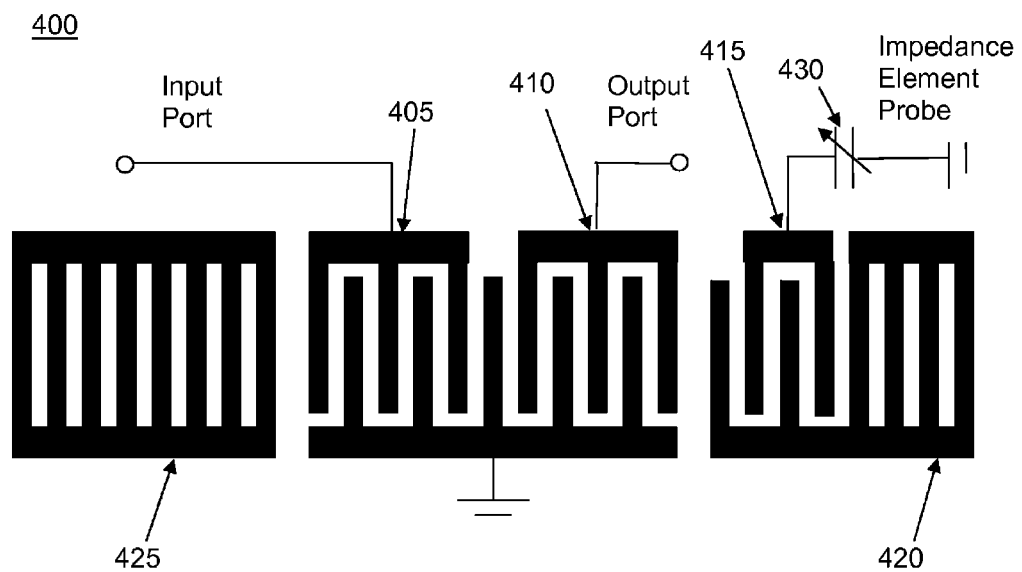
FIG. 4 is a diagram illustrating a three port SAW resonator with an external probe configured in accordance with one embodiment of the present invention.

FIG. 4 displays an embodiment 400 with a transmission based sensor (e.g. a feedback oscillator circuit) using a three IDT device consisting of an input port 405, an output port 410, a sensing port 415, plus reflectors 420 and 425. Operable connections are between an IDT (sensing port) and external impedance element probe 430. Again, any two terminal impedance element or network may be employed. Also, the arrangements of inputs, outputs, and sensing ports may be varied and more arrangements can be employed in other embodiments for specific delay line and resonator geometries including the use of a plurality of sensing ports.

Figure 5:
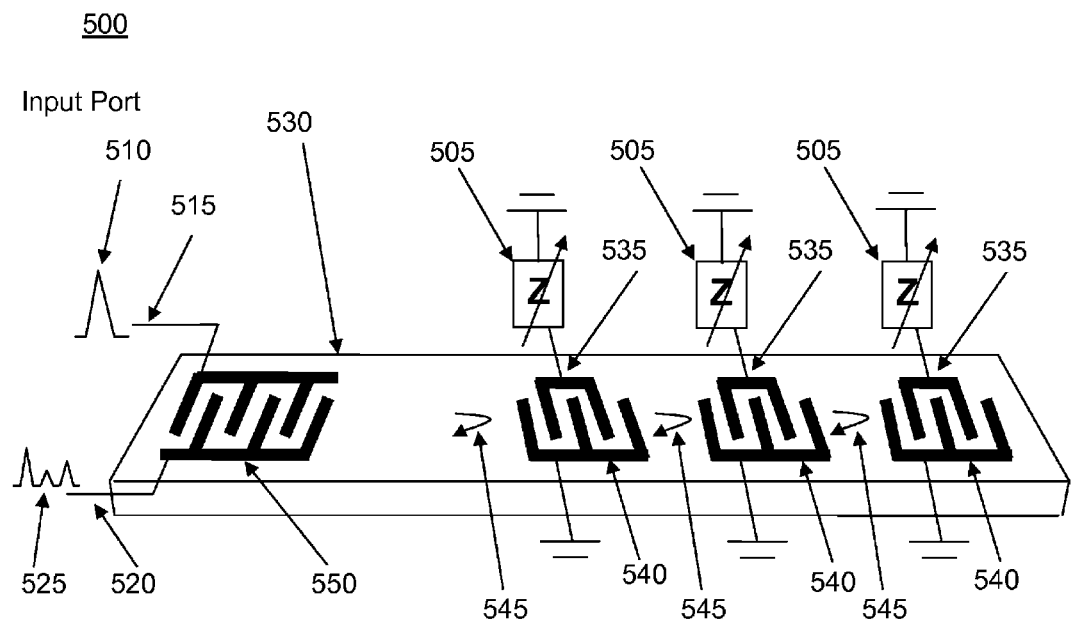
FIG. 5 is a diagram illustrating a schematic layout of a wireless interrogation passive SAW device configured in accordance with one embodiment of the present invention.

As shown in embodiment 500 of FIG. 5, the changes of external impedance element probes 505 can be addressed wirelessly by combining with a SAW transponder. The separate transceiver (not shown) emits radio frequency interrogation signals 510 that are applied to the sensor's input electrical port via antenna 515. Response antenna 520 reradiates 525 the delayed echo or modulates the continuous input signal through well-known back-scatter methods. Frequently, the same physical antenna serves both purposes. FIG. 5's schematic layout overall shows a passive SAW device 530 combined with a plurality of external impedance element probes 505 operably connected to sensor ports 535. More sensor ports 535 and IDTs 540 can be employed in embodiments. The varying impedance affects the SAW IDTs' 540 reflections' 545 behavior with IDT 550. This impacts the re-transmitted response signal 525 from the received request signal 510 of the transponder. Depicted response signal 525 shows three echoes from three reflections 545 from three IDTs 540. In one embodiment, a second interdigital transducer is connected to a second microwave antenna.

Figure 6:
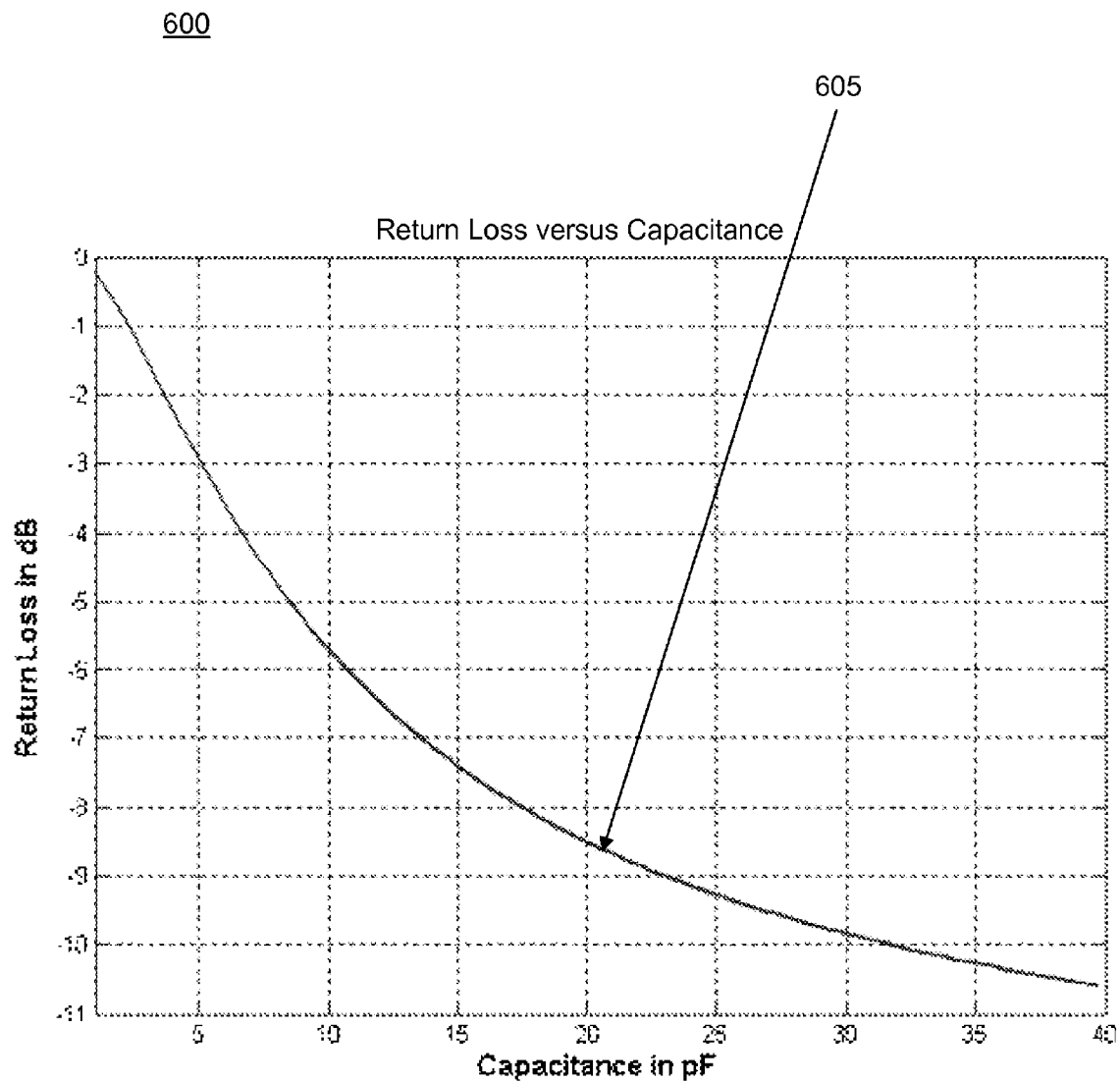
FIG. 6 is a graph of simulated Return Loss versus Capacitance for an illustrative embodiment of the invention.

FIG. 6, graph 600 depicts simulation results 605 of Return Loss versus Capacitance for a SAW resonator cascaded to an external loaded capacitance on a prototype AWD device embodiment. A linearity range is apparent between 1 and 10 pF. This device could be, for example, a one port resonator employing the variation of the values of a serial-loaded (external) magnetically-responsive capacitance.

Figure 7:
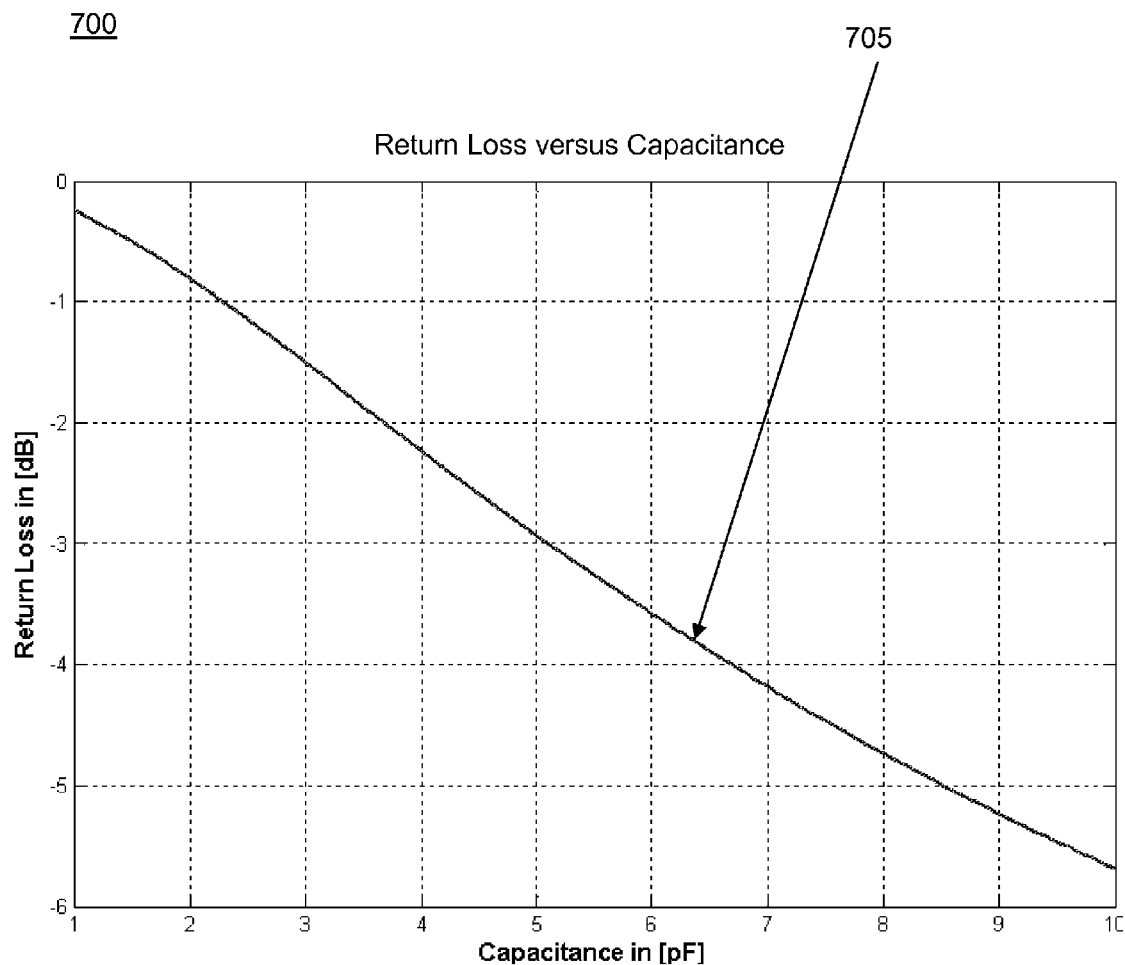
FIG. 7 is a graph 700 of simulated Return Loss versus Capacitance for a section of the graph of FIG. 6 for an illustrative embodiment of the invention. It depicts the linearity of the return loss values for capacitance values ranging from 1 to 10 pF.

FIG. 7 is a graph 700 of simulated results of Return Loss versus Capacitance 705 for a section of the graph of FIG. 6 for an illustrative embodiment of the invention. It depicts the linearity of the return loss values for capacitance values ranging from 1 to 10 pF. This can provide an expectation of the resultant return loss as a variable capacitor's capacitance changes in response to measurands.

Figure 8:
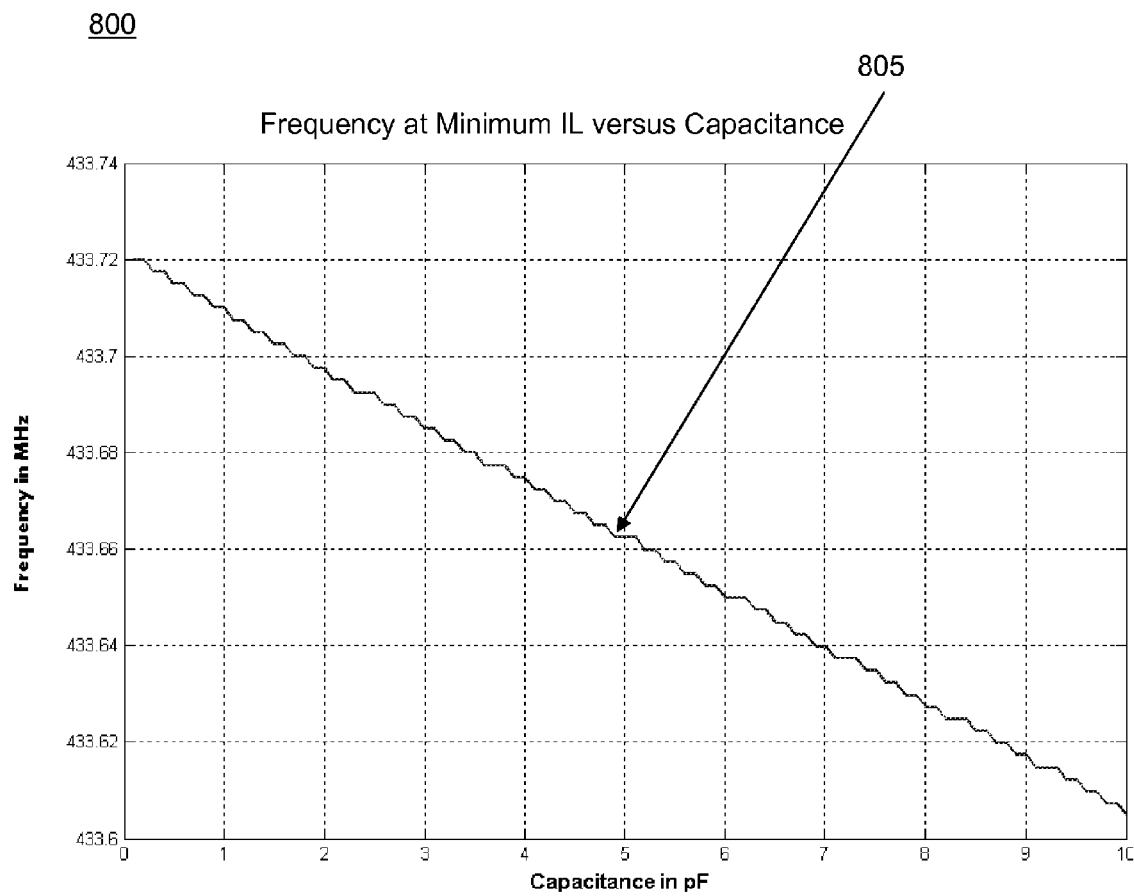
FIG. 8 is a graph of simulated Frequency at Minimum Insertion Loss versus capacitance for an illustrative embodiment of the invention.

FIG. 8 is a graph 800 of simulated results 805 showing the linearity range of the frequency change at the minimum insertion loss (IL) point versus variations of the value of the (external) parallel loaded capacitance for an illustrative embodiment. Here, the capacitance range is between 0.1 pF to 10 pF. The corresponding frequency change can be used as a sensor parameter in response to measurands.

FIGS. 9 through 14 present measured data from an illustrative embodiment. In this embodiment, the variable impedance element probe is a cantilever variable capacitor. The measurement methodology included a capacitive-metal-cantilever mounted on the input side of a SAW device (a filter at 2326 MHz) between hot and ground connections. A magnetic disk was moved toward the cantilever from a distance of 10 mm (0.39 inch). Five measurements (points 1, 2, 3, 4, and 5) were recorded in steps of 2 mm (0.079 inch). Point 1 is the initial, farthest, point from the sensor, and point 5 is the last, closest, point from the sensor. The magnetic disk dimensions were a thickness of 0.100 inch (2.54 mm) and a diameter of 0.375 inch (9.525 mm).

Figure 9:
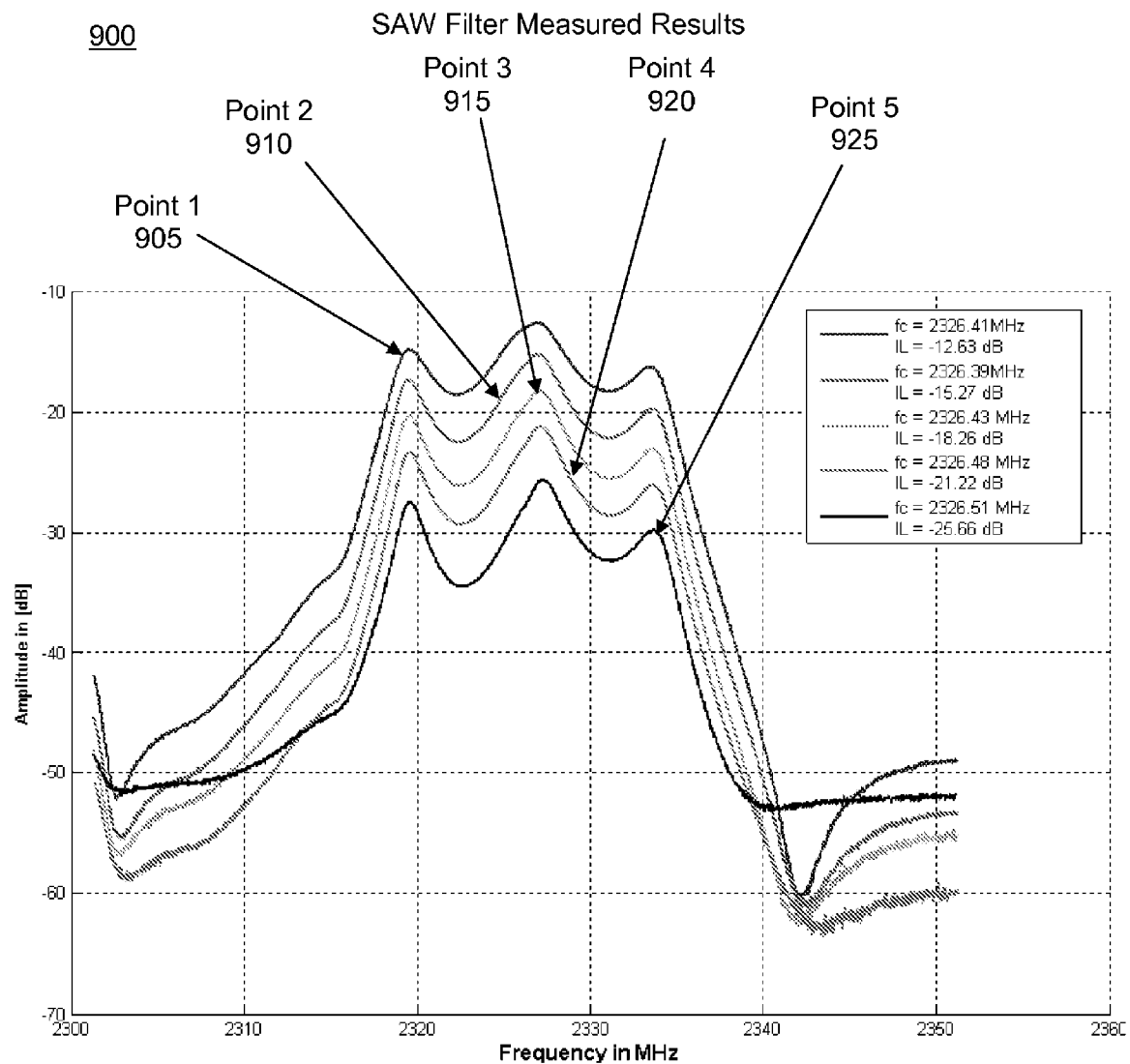
FIG. 9 is a graph of measured electrical transfer function as a function of frequency for a SAW filter for an illustrative embodiment of the invention.
Figure 10:
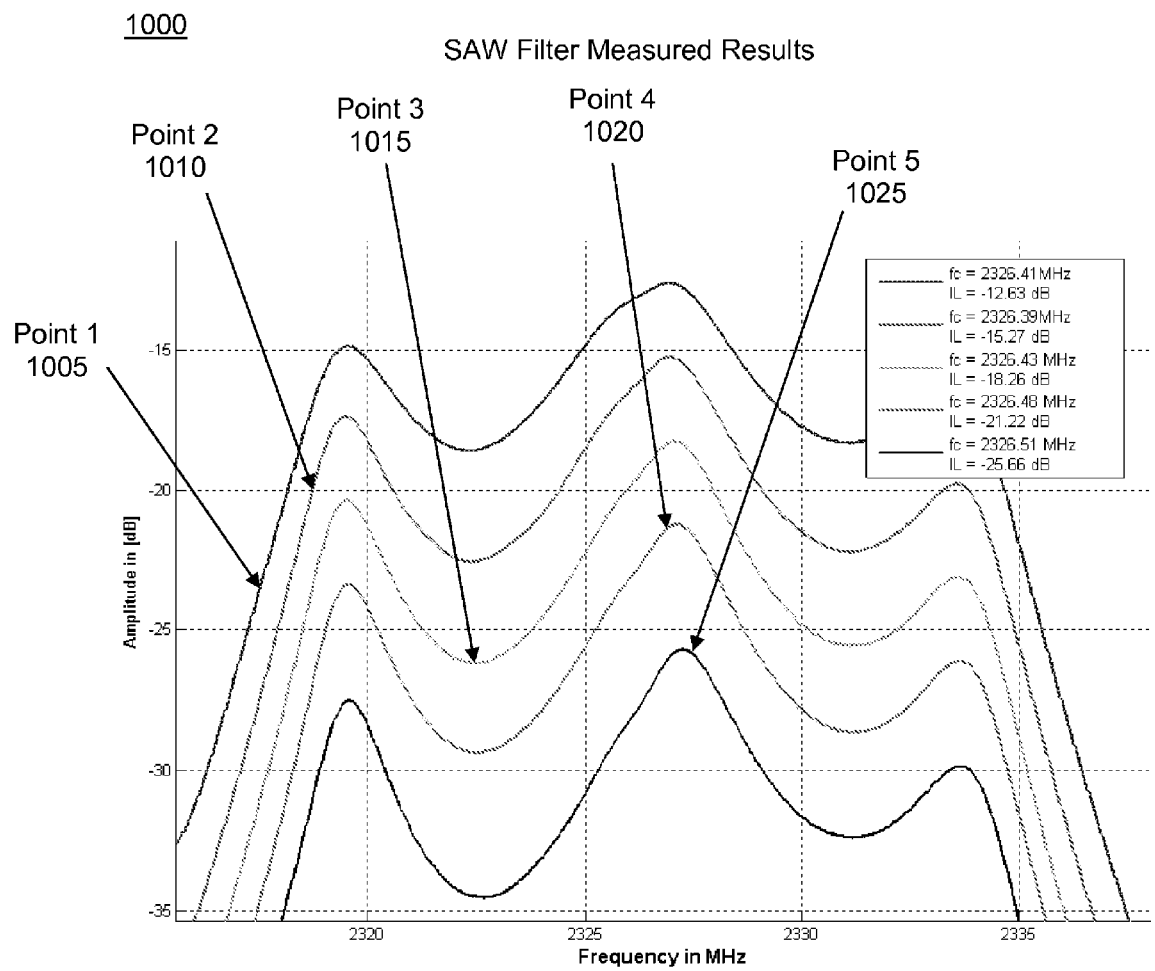
FIG. 10 is a graph of a section of the graph of FIG. 9 from 2315 to 2340 MHz.

FIGS. 9 and 10 show the measured electrical transfer function as a function of frequency for transmission responses (S21) of the SAW device versus magnetic field variation. The measured curve shows the degradation of the device insertion loss by magnetic field change.

FIG. 9 is a graph 900 of measured Insertion Loss vs. Frequency signal amplitudes as a function of frequency for a variable capacitor—SAW filter embodiment. The parameters for measurement points and curves follow. For point 1, curve 905, $f_c$=2326.41 MHz, and IL=−12.63 dB. For point 2, curve 910, $f_c$=2326.39 MHz, IL=−15.27 dB. For point 3, curve 915, $f_c$=2326.43 MHz, IL=−18.26 dB. For point 4, curve 920, $f_c$=2326.48 MHz, IL=−21.22 dB. Finally, for point 5, curve 925, $f_c$=2326.51 MHz, insertion loss (IL)=−25.66 dB.

FIG. 10 is a graph 1000 of a section of the graph of FIG. 9 showing detail from 2315 to 2340 MHz 1005. The curve and point designations correspond to those of FIG. 9. Specifically, 1005 and 905 represent the same curve as do 1015 and 915, 1010 and 910, 1015 and 915, 1020 and 920, and 1025 and 925.

Figure 11:
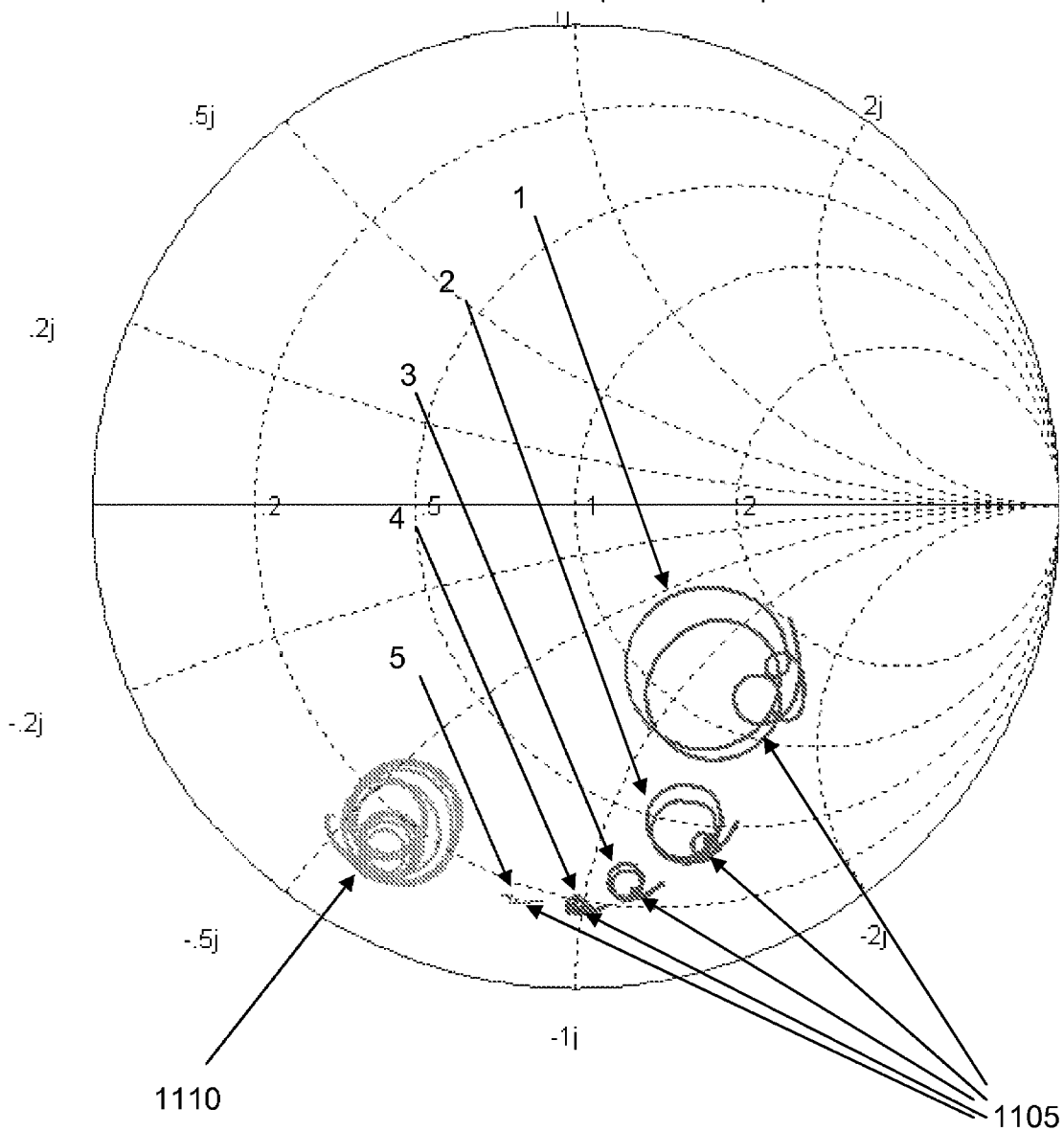
FIG. 11 is a Smith Chart of measured Input and Output reflection coefficient for an illustrative embodiment of the invention.

FIG. 11 is a Smith Chart 1100 of Input 1105 and Output reflection coefficient 1110 for the variable capacitor—SAW filter embodiment of FIGS. 9 and 10. The Smith Charts (FIGS. 11 and 12) show the impedance change at the SAW device input side (S11) where the cantilever was mounted. Data annotations 1, 2, 3, 4, and 5 correspond to the same measurements for FIGS. 9 through 14. Values for output 1110 (S22) are unchanging in this case.

Figure 12:
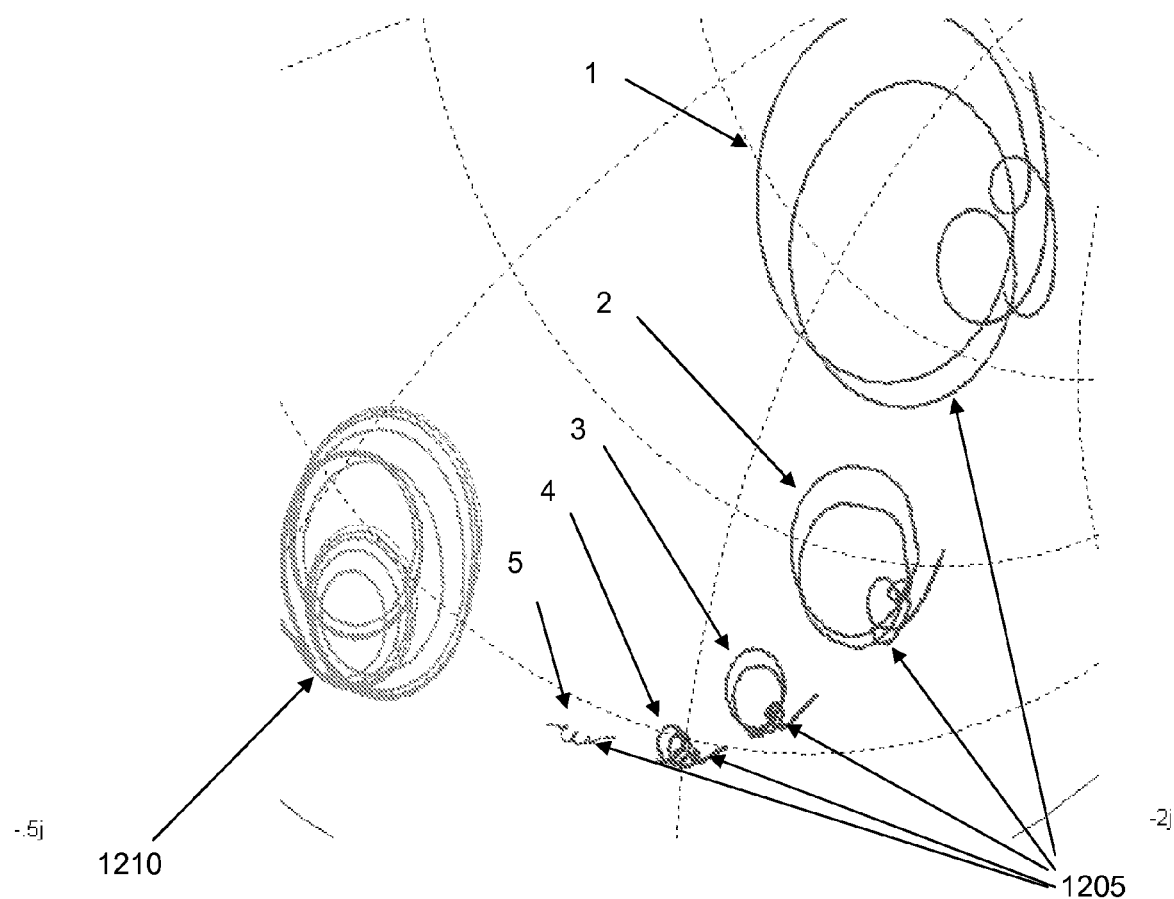
FIG. 12 is a section of the Smith Chart of FIG. 11 for measured Input and Output reflection coefficient.

FIG. 12 is a Smith Chart 1200 of an enlarged section of the Smith Chart of FIG. 11 showing more detail for measured Input 1205 and Output reflection coefficient 1210 of this variable capacitor—SAW filter embodiment.

Figure 13:
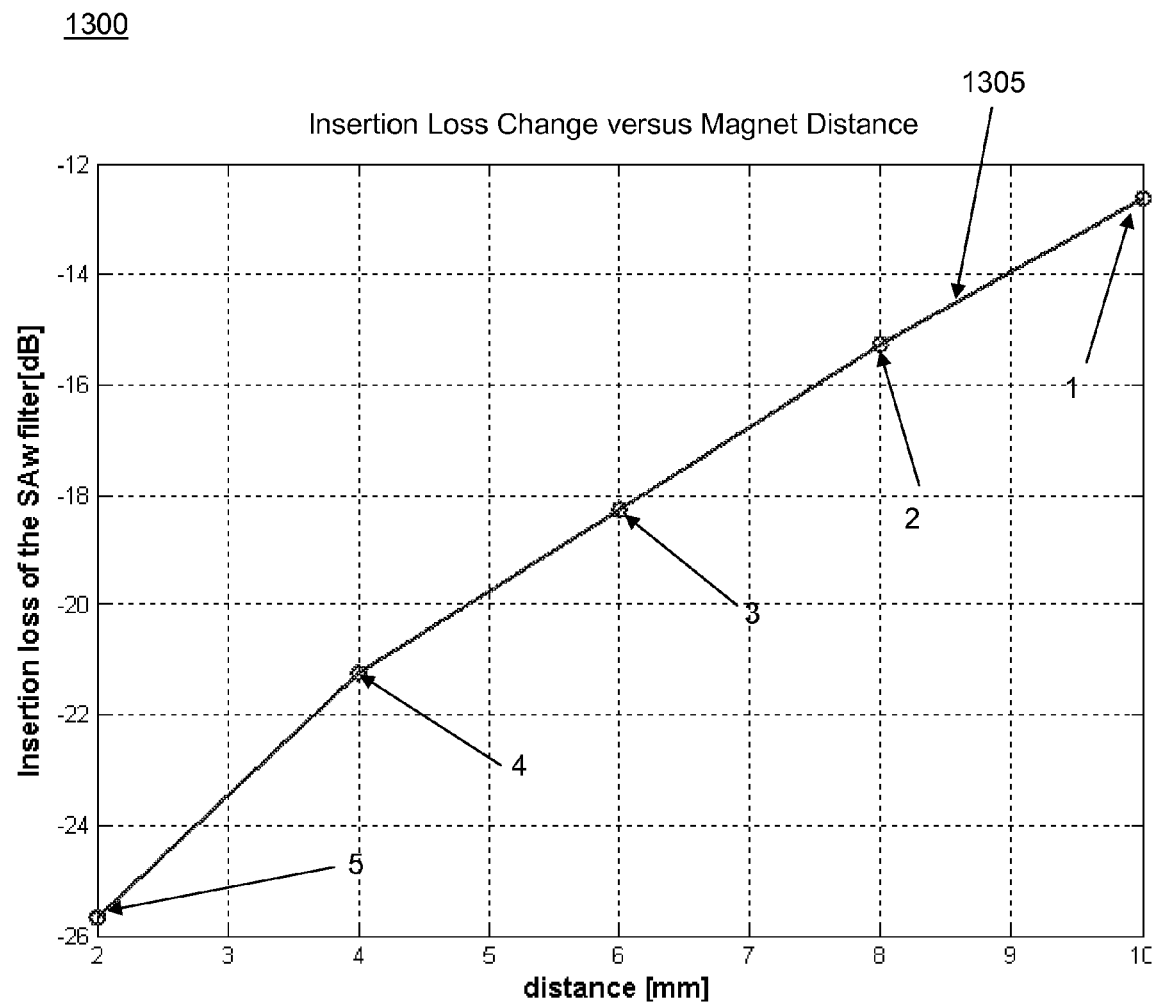
FIG. 13 is a graph of measured SAW Filter Insertion Loss Change versus Magnet Distance for an illustrative embodiment of the invention.

FIG. 13 is a graph 1300 of SAW Filter Insertion Loss Change versus Magnet Distance 130. This also is for the variable capacitor—SAW filter embodiment of FIGS. 9 through 12. As before, data annotations 1, 2, 3, 4, and 5 correspond to the same measurement points for FIGS. 9 through 14. The figure shows an approximately linear relation between the distance of the magnetic disk to the cantilever and the impedance mismatching of the SAW device resulting from the decrease of insertion loss.

Figure 14:
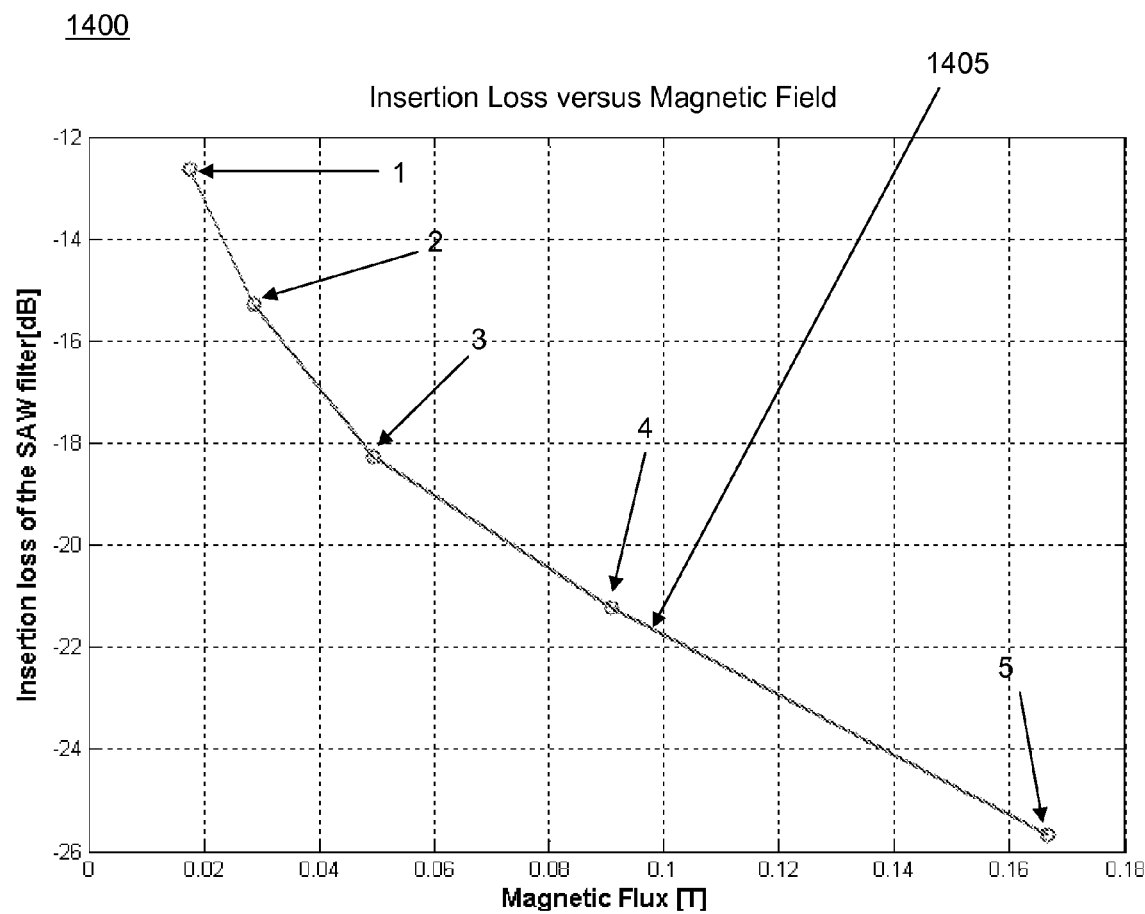
FIG. 14 is a graph of measured SAW Filter Insertion Loss versus Magnetic Field Flux for an illustrative embodiment of the invention.

FIG. 14 is a graph 1400 of SAW Filter Insertion Loss versus Magnetic Field Flux 1405, again for the variable capacitor—SAW filter embodiment of FIGS. 9 through 13. This figure also shows an approximately linear relation between the magnetic flux at the variable capacitor impedance probe and the impedance mismatching of the SAW device.

In multiple embodiments, a capacitor was stated or shown. In fact, any impedance element that is physically responsive to the measurand is suitable. One skilled in the art will intuitively expect that capacitive and inductive elements will only alter phase or frequency while resistive changes will alter amplitude. However, reactive impedance elements can significantly alter amplitude as well as phase and resistive elements can dramatically alter frequency and phase of an AWD. The passive wireless example given employed a capacitor to alter the reflected (backscattered) signal. Altering transmitted signals is equally possible. Even in the reflected signal depicted, there would be additional, unperturbed, reflections in a practical sensor in order to provide a reference value. It is also possible for the impedance element to be a one-port AWD (e.g. a BAW device) having the desired sensitivity, the impedance element transduced by the two-port AWD in order to allow a passive wireless interrogation.

The foregoing examples have identified surface acoustic wave devices with interdigital transducers (IDT) providing the electrical ports. IDTs are capable of generating other modes including such surface guided acoustic wave (SGAW) modes as Love waves, Lamb waves, Sezawa waves, Rayleigh waves, Bluestein-Gulayey and other surface-transverse waves, acoustic plate modes and surface skimming bulk waves to name a few. Nothing in the description should be deemed to restrict the invention or the meaning of acoustic wave device in the claims to any particular type of acoustic wave and the examples given shall be construed as illustrative only.

Embodiment descriptions have included interdigital transducers (IDT). Parallel plate transducers of thickness field excited bulk acoustic waves and the coplanar electrodes of lateral field excited bulk acoustic wave devices are also applicable. The use of eddy currents in a metal sheet with a biasing magnetic field or of fixed currents in a serpentine or other pattern in the magnetic field are known to induce acoustic waves and are also contemplated in the meaning of transducer or electrical port.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A system for measuring a physical measurand comprising:
    at least one variable impedance element probe responsive to at least one measurand; and
    at least one electromagnetic device (EMD) having at least one port, wherein said at least one variable impedance element probe is operably connected to said at least one port, said at least one EMD being electrically responsive to said response of said variable impedance element probe;
    wherein said at least one EMD is at least one acoustic wave device (AWD);
    wherein each of said at least one acoustic wave devices (AWDs) comprises an input port and at least one sensing port, wherein said at least one variable impedance element probe is operably connected to said at least one sensing port;
    wherein said at least one AWD is a reflective-tap delay line comprising reflective taps, wherein at least one of said reflective taps comprises at least one interdigital transducer (IDT), said IDT comprising said at least one sensing port;
    said system further comprising a plurality of said reflective taps providing an identification sequence specific to said system.

2. A system for measuring a physical measurand comprising:
    at least one variable impedance element probe responsive to at least one measurand; and
    at least one electromagnetic device (EMD) having at least one port, wherein said at least one variable impedance element probe is operably connected to said at least one port, said at least one EMD being electrically responsive to said response of said variable impedance element probe;
    wherein said at least one EMD is at least one acoustic wave device (AWD);
    wherein each of said at least one acoustic wave devices (AWDs) comprises an input port and at least one sensing port, wherein said at least one variable impedance element probe is operably connected to said at least one sensing port;
    wherein said at least one variable impedance element probe is a variable capacitor responsive to magnetic fields.

3. A system for measuring a physical measurand comprising:
    at least one variable impedance element probe responsive to at least one measurand; and
    at least one electromagnetic device (EMD) having at least one port, wherein said at least one variable impedance element probe is operably connected to said at least one port, said at least one EMD being electrically responsive to said response of said variable impedance element probe;
    wherein said at least one EMD is at least one acoustic wave device (AWD);
    wherein each of said at least one acoustic wave devices (AWDs) comprises an input port and at least one sensing port, wherein said at least one variable impedance element probe is operably connected to said at least one sensing port;
    wherein said at least one variable impedance element probe is a variable capacitor responsive to pressure.

4. A system for measuring a physical measurand comprising:
    at least one variable impedance element probe responsive to at least one measurand; and
    at least one electromagnetic device (EMD) having at least one port, wherein said at least one variable impedance element probe is operably connected to said at least one part, said at least one EMD being electrically responsive to said response of said variable impedance element probe;
    wherein said physical measurand is selected from the group consisting of: magnetic field, electric field, pressure, strain, stress, temperature, acoustic vibration, acceleration, chemical concentration, biochemical concentration, viscosity, density, and elastic modulus.

5. A system for measuring a physical measurand comprising:
    at least one variable impedance element probe responsive to at least one measurand; and
    at least one electromagnetic device (EMD) having at least one port, wherein said at least one variable impedance element probe is operably connected to said at least one port, said at least one EMD being electrically responsive to said response of said variable impedance element probe;
    wherein said variable impedance element probe is a variable capacitor, wherein said variable capacitor capacitance value changes in response to motion of one or more elements of said variable capacitor.

6. The system of claim 5, wherein said variable capacitor is selected from the group consisting of: a comb capacitor, a cantilever capacitor, and a suspended membrane capacitor.

7. A system for measuring a physical measurand comprising:
- at least one variable impedance element probe responsive to at least one measurand; and
- at least one electromagnetic device (EMD) having at least one port, wherein said at least one variable impedance element probe is operably connected to said at least one port, said at least one EMD being electrically responsive to said response of said variable impedance element probe;
- wherein said variable impedance element probe is selected from the group consisting of: a chemically responsive resistance, a chemical field-effect transistor (ChemFET), and a metal-oxide-semiconductor field-effect transistor (MOSFET).

* * * * *

UNITED STATES PATENT AND TRADEMARK OFFICE
CERTIFICATE OF CORRECTION

PATENT NO. : 7,855,564 B2
APPLICATION NO. : 12/031055
DATED : December 21, 2010
INVENTOR(S) : Sabah Sabah, Jeffrey C. Andle and Daniel S. Stevens It is certified that error appears in the above-identified patent and that said Letters Patent is hereby corrected as shown below:

Column 12
Line 45, delete "part", insert --port--

Signed and Sealed this
Thirtieth Day of August, 2011

David J. Kappos
*Director of the United States Patent and Trademark Office*